US010329250B2

(12) United States Patent
Ujihara et al.

(10) Patent No.: US 10,329,250 B2
(45) Date of Patent: Jun. 25, 2019

(54) PROCESS FOR PRODUCING 7-DEHYDROCHOLESTEROL AND VITAMIN D3

(71) Applicant: KYOWA HAKKO BIO CO., LTD., Tokyo (JP)

(72) Inventors: Tetsuro Ujihara, Tokyo (JP); Satoshi Mitsuhashi, Tokyo (JP)

(73) Assignee: KYOWA HAKKO BIO CO., LTD., Tokyo (JP)

( * ) Notice: Subject to any disclaimer, the term of this patent is extended or adjusted under 35 U.S.C. 154(b) by 179 days.

(21) Appl. No.: 15/515,142

(22) PCT Filed: Oct. 8, 2015

(86) PCT No.: PCT/JP2015/078560
§ 371 (c)(1),
(2) Date: Mar. 28, 2017

(87) PCT Pub. No.: WO2016/056610
PCT Pub. Date: Apr. 14, 2016

(65) Prior Publication Data
US 2017/0204056 A1     Jul. 20, 2017

(30) Foreign Application Priority Data
Oct. 8, 2014  (JP) ................................ 2014-207009

(51) Int. Cl.
| C12N 9/10 | (2006.01) |
| C07C 401/00 | (2006.01) |
| C12P 33/00 | (2006.01) |
| B01J 19/12 | (2006.01) |
| C12P 7/22 | (2006.01) |
| C12N 15/09 | (2006.01) |

(52) U.S. Cl.
CPC ........... *C07C 401/00* (2013.01); *B01J 19/123* (2013.01); *C12N 9/1007* (2013.01); *C12P 7/22* (2013.01); *C12P 33/00* (2013.01); *C12Y 201/01041* (2013.01); *B01J 2219/12* (2013.01); *C12N 15/09* (2013.01)

(58) Field of Classification Search
CPC ........................... C12N 15/8247; C07K 14/09
USPC ....................................... 435/195, 212, 219
See application file for complete search history.

(56) References Cited

U.S. PATENT DOCUMENTS

| 6,180,805 B1 | 1/2001 | Jansen |
| 2006/0240508 A1 | 10/2006 | Lang et al. |
| 2009/0239837 A1 | 9/2009 | Pompon et al. |
| 2016/0332964 A1 | 11/2016 | Ujihara et al. |

FOREIGN PATENT DOCUMENTS

| DE | 10203352 A1 | 7/2003 |
| JP | 2000-026405 A | 1/2000 |
| JP | 2004-141125 A | 5/2004 |
| JP | 2007-535960 A | 12/2007 |
| WO | WO 2008/130372 A2 | 10/2008 |
| WO | WO 2011/067144 A1 | 6/2011 |
| WO | WO 2015/108058 A1 | 7/2015 |

OTHER PUBLICATIONS

Huang et al., "Expressed sequence tag analysis of marine fungus *Schizochytrium* producing docosahexaenoic acid," *J. Biotechnol.*, 138(1-2): 9-16 (2008).
Pereira et al., "Cloning, mechanistic and functional analysis of a fungal sterol C24-methyltransferase implicated in brassicasterol biosynthesis," *Biochim. Biophys. Acta*, 1801(10): 1163-1174 (2010).
European Patent Office, Extended European Search Report in European Patent Application No. 15848702.5 (dated Mar. 23, 2018).
Wang et al., "Characterization of Lipid Components in Two Microalgae for Biofuel Application," *J. Am Oil Soc.*, 89: 135-143 (2012).
Weete et al., "Fatty Acids and Sterols of Selected Hyphochytriomycetes and Chytridiomycetes," *Experimental Mycology*, 13: 183-195 (1989).
Weete et al., "Lipids and Ultrastructure of *Thraustochytrium* sp. ATCC 26185," *Lipids*, 32(8): 839-845 (1997).
Yamaoka et al., "Production of Useful Substances by the Protist *Thraustochytrium* (labyrinthulids) Isolated from the Seto Inland Sea," *Bulletin of the Society of Sea Water Science*, Japan, 59: 32-39 (2005).
Japanese Patent Office, International Search Report in International Patent Application No. PCT/JP2015/078560 (dated Dec. 15, 2015).
Ujihara et al., "Production of Non-animal Derived Vitamin D₃ by Using a Genetically Engineered Microalgae *Aurantiochytrium* sp. strain," *Abstracts of the 105th AOCS Annual Meeting & Expo*, BIO-P: Biotechnology Poster Session, Abstract No. 13 at p. 22 (May 4-May 7, 2014).
European Patent Office, Communication Pursuant to Article 94(3) EPc in European Patent Application No. 15848702.5 (dated Dec. 17, 2018).

*Primary Examiner* — Tekchand Saidha
(74) *Attorney, Agent, or Firm* — Leydig, Voit & Mayer, Ltd.

(57) ABSTRACT

According to the present invention, there can be provided a process for producing 7-dehydrocholesterol (7DHC), comprising culturing, in a medium, a 7DHC-producing *Labyrinthulea* microorganism in which sterol 24-C-methyltransferase activity is reduced or lost as compared to a parent strain, allowing 7DHC to be produced and accumulated in the culture, and collecting the 7DHC from the culture; and a process for producing vitamin D3, comprising irradiating, with ultraviolet light, 7-dehydrocholesterol produced by the production process.

6 Claims, 1 Drawing Sheet
Specification includes a Sequence Listing.

PROCESS FOR PRODUCING 7-DEHYDROCHOLESTEROL AND VITAMIN D3

CROSS-REFERENCE TO RELATED APPLICATIONS

This patent application is the U.S. national phase of International Patent Application No. PCT/JP2015/078560, filed Oct. 8, 2015, which claims the benefit of Japanese Patent Application No. 2014-207009, filed on Oct. 8, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,534 bytes ASCII (Text) file named "728152SequenceListing.txt," created Mar. 23, 2017.

TECHNICAL FIELD

The present invention relates to a process for producing 7-dehydrocholesterol (hereinafter, also referred to as "7DHC") using *Labyrinthulea* microorganisms, and to a process for producing vitamin D3 comprising irradiating, with ultraviolet light, the 7DHC produced by the production process.

BACKGROUND ART

Vitamin D3 is a vitamin involved in various functions including metabolism and homeostasis maintenance of calcium and phosphorus, and bone formation, and is produced from cholesterol in the human body. However, because the quantity of vitamin D3 produced in the body is smaller than the required quantities, vitamin D3 needs to be ingested through food, drug products, or supplements.

Vitamin D3 contained in drug products and supplements is produced mainly through ultraviolet irradiation of 7DHC produced by chemical transformation from cholesterol obtained from wool. However, use of animal-derived materials as source materials of drug products and supplements tends to be avoided due to the concerns of BSE and zoonosis, and there is a need for vitamin D3 derived from non-animal. Vitamin D3 derived from non-animals can be produced through ultraviolet irradiation of 7DHC derived from non-animal.

Generally, a sterol biosynthesized by microorganisms is ergosterol. However, some members of *Labyrinthulea* microorganisms are known to biosynthesize cholesterol (Non-Patent Documents 1 to 3). 7DHC is converted into cholesterol by 7DHC reductase. However, although the *Labyrinthulea* microorganisms accumulate cholesterol, there is no report that *Labyrinthulea* microorganisms accumulate 7DHC.

Sterol 24-C-methyltransferase has an activity to introduce a methyl group at the 24-position of a steroid backbone of zymosterol (hereinafter referred to as "sterol 24-C-methyltransferase activity" or "SMT activity"). The SMT activity is essential for the biosynthesis of ergosterol, but is not involved in the biosynthesis of cholesterol.

Further, there is no report that *Labyrinthulea* microorganisms which biosynthesize cholesterol have SMT activity, and produce and accumulate 7DHC by reducing or eliminating the SMT activity.

RELATED ART

Non-Patent Document

Non-Patent Document 1: Exp. Mycol. (1989) 13:183-195
Non-Patent Document 2: Lipids (1997) 32:839-845
Non-Patent Document 3: J. Am. Oil Chem. Soc. (2012) 89:135-143

DISCLOSURE OF INVENTION

Problems to be Solved by the Invention

It is an object of the present invention to provide a process for efficiently producing 7DHC using a *Labyrinthulea* microorganism, and a process for producing vitamin D3 comprising irradiating, with ultraviolet light, 7DHC produced by the production process.

Means for Solving the Problems

The present invention relates to the following (1) to (6).
(1) A process for producing 7-dehydrocholesterol (hereinafter, "7DHC"), comprising:
  culturing, in a medium, a 7DHC-producing *Labyrinthulea* microorganism in which sterol 24-C-methyltransferase activity (hereinafter, "SMT activity") is reduced or lost as compared to a parent strain;
  allowing 7DHC to be produced and accumulated in the culture; and
  collecting the 7DHC from the culture.
(2) The production process described in (1) above, wherein the *Labyrinthulea* microorganism in which the SMT activity is reduced or lost as compared to the parent strain is a *Labyrinthulea* microorganism in which the SMT activity is reduced or lost as compared to the parent strain through deletion, substitution, or addition of at least one base in a gene which is present in the chromosomal DNA of the parent strain and encodes a protein having SMT activity.
(3) The production process described in (1) above, wherein the *Labyrinthulea* microorganism in which the SMT activity is reduced or lost as compared to the parent strain is a *Labyrinthulea* microorganism in which the SMT activity is reduced or lost as compared to the parent strain, being obtained by transforming the parent strain with a DNA encoding an RNA which has a sequence complementary to a messenger RNA transcribed from a gene present in the chromosomal DNA of the parent strain and encoding a protein having SMT activity, and forms a conjugate with the messenger RNA.
(4) The production process described in (2) or (3) above, wherein the gene encoding a protein having SMT activity is a gene having any of the following DNAs [1] to [5]:
  [1] a DNA encoding a protein having the amino acid sequence represented by SEQ ID NO: 2;
  [2] a DNA encoding a homologous protein having at least 95% identity with the amino acid sequence represented by SEQ ID NO: 2, and having SMT activity;
  [3] a DNA having the base sequence represented by SEQ ID NO: 1;
  [4] a DNA that hybridizes with a DNA consisting of a base sequence complementary to the base sequence represented by SEQ ID NO: 1 under stringent conditions, and encodes a homologous protein having SMT activity; and

[5] a DNA having at least 95% identity with the base sequence represented by SEQ ID NO: 1, and encoding a homologous protein having SMT activity.

(5) The production process described in any one of (1) to (4) above, wherein the *Labyrinthulea* microorganism is a *Labyrinthulea* microorganism of the genus *Schizochytorium, Thraustochytrium, Aurantiochytrium, Parietichytrium, Labyrinthula, Althornia, Aplanochytrium, Japonochytrium, Labyrinthuloides, Ulkenia, Oblongichytrium, Botryochytrium*, or *Sicyoidochytrium*.

(6) A process for producing vitamin D3, comprising irradiating the 7DHC produced by the production process described in any one of (1) to (5) above with ultraviolet light.

Effects of the Invention

According to the present invention, a process for efficiently producing 7DHC using a *Labyrinthulea* microorganism, and a process for producing vitamin D3 comprising irradiating, with ultraviolet light, 7DHC produced by the production process can be provided.

EMBODIMENTS FOR CARRYING OUT THE INVENTION

1. *Labyrinthulea* Microorganism Used in Production Process of the Present Invention The *Labyrinthulea* microorganism used in the production process of the present invention is a 7DHC-producing *Labyrinthulea* in which the SMT activity is reduced or lost as compared to a parent strain.

Here, "parent strain" means an original strain subjected to gene modification, transformation, and the like. An original strain subjected to transformation by gene introduction is also called "host strain".

The parent strain is not particularly limited, as long as it is a *Labyrinthulea* microorganism having the SMT activity and capable of producing cholesterol or 7DHC to such an extent that it can be collected from cells or medium after culture in a medium. Preferred examples include *Labyrinthulea* microorganisms of the genus *Schizochytrium, Thraustochytrium, Aurantiochytrium, Parietichytrium, Labyrinthula, Althornia, Aplanochytrium, Japonochytrium, Labyrinthuloides, Ulkenia, Oblongichytrium, Botryochytrium*, or *Sicyoidochytrium*. More preferred examples include *Labyrinthulea* microorganisms of the genus *Schizochytorium, Thraustochytrium, Aurantiochytrium*, or *Parietichytrium*. Further preferred examples include *Aurantiochytrium limacinum* ATCC MYA-1381, *Thraustochytrium aureum* ATCC34304, *Thraustochytrium* sp. ATCC26185, *Schizochytrium* sp. AL1Ac, *Schizochytrium aggregatum* ATCC28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 (FERM ABP-11298). Most preferred examples include *Aurantiochytrium limacinum* ATCC MYA-1381.

The SMT activity refers to an activity to introduce a methyl group at the 24-position of a steroid backbone of zymosterol.

Examples of the *Labyrinthulea* microorganism in which the SMT activity is reduced or lost as compared to a parent strain include a *Labyrinthulea* microorganism in which the SMT activity is reduced or lost as compared to a parent strain through deletion, substitution, or addition of at least one base in a gene which is present in the chromosomal DNA of the parent strain and encodes a protein having SMT activity, and a *Labyrinthulea* microorganism in which the SMT activity is reduced or lost as compared to a parent strain, being obtained by transforming the parent strain with a DNA encoding an RNA which has a sequence complementary to a messenger RNA transcribed from the gene and forms a conjugate with the messenger RNA.

The "protein having SMT activity" is not limited, as long as it is a protein encoded by a gene in a genomic chromosome of a *Labyrinthulea* microorganism, and having SMT activity, but is preferably the following protein [1] or [2]:

[1] a protein having the amino acid sequence represented by SEQ ID NO: 2; or

[2] a homologous protein having at least 95%, preferably at least 97%, more preferably at least 98%, most preferably at least 99% identity with the amino acid sequence represented by SEQ ID NO: 2, and having SMT activity.

The "homologous protein" refers to a protein which is possessed by organisms found in nature, and is encoded by a gene that is believed to share the same evolutional origin with a gene encoding an original protein because the homologous protein has a structure and functions similar to those of the original protein.

The identify of the amino acid sequences and base sequences can be determined using the algorithm BLAST [Pro. NATdomainl. Acad. Sci. USA, 90, 5873(1993)] by Karlin and Altschul, and FASTA [Methods Enzymol., 183, 63 (1990)]. Programs called BLASTN and BLASTX based on the algorithm BLAST have been developed [J. Mol. Biol., 215, 403(1990)]. For analysis of base sequences using BLASTN based on BLAST, the parameters are, for example, Score=100, and word length=12. For analysis of amino acid sequences using BLASTX based on BLAST, the parameters, for example, score=50, and word length=3. When using BLAST and Gapped BLAST programs, the programs are used with their default parameters. Specific techniques for these analysis methods are known.

The "gene encoding a protein having SMT activity" is not limited, as long as it is a gene present on a genomic chromosome of a *Labyrinthulea* microorganism, and encodes a protein having SMT activity, but is preferably a gene having any of the following DNAs [3] to [6]:

[3] a DNA encoding the protein [1] or [2] above;

[4] a DNA having the base sequence represented by SEQ ID NO: 1;

[5] a DNA that hybridizes with a DNA consisting of a base sequence complementary to the base sequence represented by SEQ ID NO: 1 under stringent conditions, and encodes a homologous protein having SMT activity; and

[6] a DNA having at least 95%, preferably at least 97%, more preferably at least 98%, most preferably at least 99% identity with the base sequence represented by SEQ ID NO: 1, and encoding a homologous protein having SMT activity.

The "gene" refers to a DNA which may comprise, in addition to a protein coding region, a transcriptional regulatory region, a promoter region, a terminator region, and the like.

The term "hybridize" means that a DNA having a specific base sequence, or a part of the DNA forms a conjugate with other DNA in a complementary fashion. Accordingly, a DNA of a specific base sequence, or a partial base sequence of the DNA may be a DNA that is useful as a probe for northern blot or southern blot analysis, or a DNA of a length that can be used as an oligonucleotide primer for PCR analysis. Examples of the DNA used as a probe include the DNA of at least 100 bases, preferably at least 200 bases, more preferably at least 500 bases. Examples of the DNA used as a primer includes the DNA of at least 10 bases, preferably at least 15 bases.

DNA hybridization experimental techniques are well known. For example, experiments may be conducted after setting hybridization conditions according standard textbooks, including Molecular Cloning, Second Edition, Third Edition (2001), Methods for GenERdomainal and Molecular BactEriology, ASM Press (1994), and Immunology methods manual, Academic press (Molecular).

Further, also according to an instructional manual accompanying a commercially available hybridization kit, a DNA which hybridizes under stringent conditions can be obtained. The commercially available hybridization kit may include, for example, Random Primed DNA Labeling Kit (manufactured by Roche Diagnostics GmbH), with which a probe is produced by a random prime method, and hybridization is performed under stringent conditions, and the like.

The above-described stringent conditions may include conditions in which a filter on which a DNA has been immobilized and a probe DNA are incubated overnight at 42° C. in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l of a denatured salmon sperm DNA, and then the filter is washed in, for example, a 0.2×SSC solution at about 65° C.

The above-described various conditions can also be set by adding or changing a blocking reagent to be used for suppressing the background in the hybridization experiment. The addition of the blocking reagent may be accompanied by a change in hybridization conditions for adapting the conditions.

The DNA which can hybridize under the above-described stringent conditions may include a DNA consisting of a nucleotide sequence having at least 95% or more, preferably 97% or more, more preferably 98% or more, and most preferably 99% or more identity to the base sequence represented by SEQ ID NO:1 when performing calculation based on the above-described parameters using, for example, the program such as BLAST or FASTA described above.

With respect to the introduction of deletion, substitution, or addition of at least one base into the gene that encodes a protein having SMT activity, the number and the type of base are not limited, as long as the deletion, substitution, or addition of at least one base makes the SMT activity weaker than in the parent strain, or eliminates the SMT activity. However, examples thereof include in the promoter and the transcriptional regulatory region, the deletion of at least one base, preferably at least 10 bases, more preferably at least 20 bases, further preferably the entire region; in the coding region, deletion of at least one base, preferably at least 10 bases, more preferably at least 20 bases, further preferably at least 100 bases, particularly preferably at least 200 bases, most preferably the entire region of the coding region.

The substitution of one or more bases may be a substitution that introduces a nonsense codon through substitution of at least one base within 150 bases, preferably 100 bases, more preferably 50 bases, particularly preferably 30 bases, most preferably 20 bases from the 5' end of the coding region.

The addition of at least one base may be an addition of a DNA fragment of at least one base, preferably at least 50 bases, more preferably at least 100 bases, further preferably at least 200 bases, particularly preferably at least 500 bases, most preferably at least 1 kb immediately after a base within 150 bases, preferably 100 bases, more preferably 50 bases, particularly preferably 30 bases, most preferably 20 bases from the 5' end of the coding region. Most preferably, the addition of one or more bases is an insertion of a gene such as a hygromycin resistant gene.

Examples of the RNA which has a sequence complementary to a messenger RNA transcribed from a gene encoding a protein having SMT activity and forms a conjugate with the messenger RNA include an RNA which forms a conjugate with the messenger RNA in 10 to 300 bases, preferably 10 to 200 bases, most preferably 10 to 100 bases. The position where a conjugate is formed in a complementary manner in the messenger RNA may be any position as long as translation from the messenger RNA is inhibited, but is preferably the 5'-terminal side of the messenger RNA.

To the RNA which forms a conjugate with the messenger RNA in a complementary manner, an RNA which forms a higher order structure for inhibiting the translation may be added.

To a DNA encoding the RNA which forms a conjugate with the messenger RNA in a complementary manner, a promoter and a terminator for transcribing the DNA in a *Labyrinthulea* microorganism may be added.

Examples of such a promoter and a terminator include pyruvate kinase promoter and actin terminator described in Example 1.

A reduction or a loss of SMT activity as compared to the parent strain can be confirmed by, for example, quantifying the amount of the transcript of the DNA of any of [3] to [6] above by northern analysis or RT-PCR, and comparing the result with the parent strain; quantifying the yield of the protein of [1] or [2] above by SDS-PAGE or an assay using an antibody, and comparing the result with the parent strain; or comparing the amount of by-produced sterols produced by the *Labyrinthulea* microorganism of the present invention with that of the parent strain according to the method described in Example 2.

Being capable of producing 7DHC means the possession of capability to produce 7DHC to such an extent that the 7DHC can be collected from the cells or medium of a cultured *Labyrinthulea* microorganism in which SMT activity is reduced or lost as compared to the above-mentioned parent strain.

2. Method of Production of *Labyrinthulea* Microorganism Used in Production Process of the Present Invention The *Labyrinthulea* microorganism used in the production process of the present invention may be produced by reducing or eliminating the SMT activity as compared to the parent strain through deletion, substitution, or addition of at least one base in a gene which is present in chromosomal DNA of the parent strain and has the DNA of any of [3] to [6].

The method for introducing the deletion, substitution, or addition of at least one base into a gene which is present in chromosomal DNA of the parent strain is not limited, and ordinary methods such as common mutagenesis, gene substitution methods using recombinant DNA techniques, and the like may be used, as long as a mutation can be introduced into chromosomal DNA of the *Labyrinthulea* microorganism.

The parent strain may be a wild-type strain, provided that it is a *Labyrinthulea* microorganism capable of producing cholesterol, and having SMT activity. When the wild-type strain lacks the cholesterol producing capability, the parent strain may be a breeding strain that has been artificially endowed with the cholesterol producing capability.

The *Labyrinthulea* microorganism may be artificially endowed with the cholesterol producing capability by using, for example, the following methods:

(a) a method that weakens or cancels at least one of the mechanisms controlling the cholesterol biosynthesis;

(b) a method that enhances the expression of at least one of the enzymes involved in the cholesterol biosynthesis;

(c) a method that increases the copy number of at least one of the enzyme genes involved in the cholesterol biosynthesis; and (d) a method that selects a cell line having higher resistance to cholesterol analogs as compared to the wild-type strain.

These known methods may be used alone or in combination.

The parent strain that can be used to prepare the *Labyrinthulea* microorganism having a cholesterol producing capability may be any strain, as long as it is a *Labyrinthulea* microorganism to which the foregoing methods (a) to (d) are applicable. Preferred examples include *Labyrinthulea* microorganisms of the genus *Schizochytrium, Thraustochytrium, Aurantiochytrium, Parietichytrium, Labyrinthula, Althornia, Aplanochytrium, Japonochytrium, Labyrinthuloides, Ulkenia, Oblongichytrium, Botryochytrium,* and *Sicyoidochytrium*. More preferred examples include *Labyrinthulea* microorganisms of the genus *Schizochytorium, Thraustochytrium, Aurantiochytrium,* and *Parietichytrium*. Further preferred examples include *Aurantiochytrium limacinum* ATCC MYA-1381, *Thraustochytrium aureum* ATCC34304, *Thraustochytrium* sp. ATCC26185, *Schizochytrium* sp. AL1Ac, *Schizochytrium aggregatum* ATCC28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 (FERM ABP-11298). Most preferred examples include *Aurantiochytrium limacinum* ATCC MYA-1381.

Mutagenesis may be achieved, for example, by a method that uses N-methyl-N'-nitro-N-nitrosoguanidine (NTG) (Microorganism Experiment Manual, 1986, p. 131, Kodansha Scientific), by ultraviolet irradiation, or the like.

As an example of gene substitution methods using recombinant DNA techniques, a recombinant DNA is created by introducing substitution, deletion, or addition of at least one base to a gene in vitro, and the recombinant DNA is introduced into the parent strain to substitute the gene originally present on the chromosome through, for example, homologous recombination or the like.

The DNAs of [3] to [6] above may be obtained by, for example, PCR using an oligoDNA designed and synthesized from the base sequence represented by SEQ ID NO: 1, and using a template chromosomal DNA prepared from a *Labyrinthulea* microorganism, according to the method of Saito et al. [BIOCHIMICA ET BIOPHYSICA ACTA (1963) 72:619-629].

Examples of the specific DNA that can be obtained include DNA having the base sequence represented by SEQ ID NO: 1.

The DNA may also be obtained by using a hybridization method that uses a part of or all of the DNA as a probe, a method that chemically synthesizes DNA having the base sequence using known techniques, or the like.

The DNA of [3] above that encodes the homologous protein of [2] above, and the DNAs that encodes the homologous proteins of [5] and [6] may be obtained by, for example, searching various gene sequence databases for a base sequence having at least 95%, preferably at least 97%, further preferably at least 98%, most preferably at least 99% identity with the base sequence represented by SEQ ID NO: 1, or searching various protein sequence databases for an amino acid sequence having at least 95%, preferably at least 97%, further preferably at least 98%, most preferably at least 99% identity with the amino acid sequence represented by SEQ ID NO: 2, and performing the same methods used to obtain the DNAs above, using a probe DNA or a primer DNA that can be designed from the base sequence or the amino acid sequence obtained after the search, and a microorganism having the DNA.

The base sequence of DNA may be determined through analysis with a base sequence analyzer, such as a 373A DNA Sequencer (manufactured by PerkinElmer Co., Ltd.), using an ordinary base-sequence analysis method, for example, such as the dideoxy method [PROCEEDINGS OF THE NATIONAL ACADEMY OF SCIENCES (1977) 74(12): 5463-5467].

When the DNA obtained is found to be a partial-length DNA after the determination of its base sequence, a full-length DNA may be obtained by using techniques such as southern hybridization with a chromosomal DNA library, using the partial-length DNA as a probe.

Such techniques are described in, for example, Molecular Cloning: A Laboratory Manual, 3rd ed., Cold Spring Harbor Laboratory Press (2001) [Hereinafter, simply "Molecular Cloning, 3rd Ed."], Current Protocols in Molecular Biology, John Wiley & Sons (1987-1997) (hereinafter, simply "Current Protocols in Molecular Biology"), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), J. Bacteriol., 182, 6884 (2000), Gene 77: 61-68, 1989, and the like.

Any method may be used for the introduction of the recombinant DNA into the parent strain, provided that the DNA can be introduced into a *Labyrinthulea* microorganism. Examples of such methods include electroporation [Appl. Microbiol. Biotech., 52, 541 (1999)], and the protoplast method [J. Bacteriol., 159, 306 (1984)].

While gene substitution on a chromosome of the parent strain can be achieved with methods such as above, the method is not limited to these, and other gene substitution methods are also usable, provided that a gene on a chromosome of a *Labyrinthulea* microorganism can be substituted.

By introducing deletion, substitution, or addition of at least one base in a gene on a chromosome of the parent strain, the activity of the protein encoded by the gene can be reduced or eliminated with good probability [An Introduction to Genetic Analysis. 7th edition (2000), Griffiths A J F, Miller J H, Suzuki D T et al., New York: W. H. Freeman].

Further, the *Labyrinthulea* microorganism used in the production process of the present invention may also be produced by transforming the parent strain with a DNA encoding an RNA which has a sequence complementary to a messenger RNA transcribed from a gene encoding a protein having SMT activity and forms a conjugate with the messenger RNA.

The DNA encoding an RNA which has a sequence complementary to the messenger RNA and forms a conjugate with the messenger RNA can be prepared by, for example, allowing an oligoDNA synthesized based on the base sequence of the RNA and an oligoDNA which forms a conjugate with the oligoDNA in a complementary manner to hybridize with each other.

In order to produce an RNA which has a sequence complementary to a messenger RNA transcribed from a gene encoding a protein having SMT activity and forms a conjugate with the messenger RNA in a cell of the *Labyrinthulea* microorganism, for example, it is also possible to add pyruvate kinase promoter and actin terminator to the DNA according to the method described in Example 1.

Examples of the method for transforming the parent strain include a method for substituting a chromosomal DNA region which does not have an influence on the production of 7DHC with the DNA using a gene substitution method through the recombinant DNA technique described above, or the like.

Production and accumulation of 7DHC in a cultured medium of a *Labyrinthulea* microorganism created by using the foregoing methods can be confirmed by homogenizing the *Labyrinthulea* microorganism with, for example, a ultrasonic or a Dyno-Mill after separating the cells from the culture, and detecting the 7DHC present in the extract by gas chromatography after solvent extraction with, for example, chloroform, hexane, butanol, or the like.

3. 7DHC Production Process of the Present Invention

A 7DHC production process of the present invention is a process for producing 7DHC which comprises culturing the *Labyrinthulea* microorganism created by using the methods in Section 2 above in a medium, and allow 7DHC to be produced and accumulated in the medium, and collecting the 7DHC from the culture.

The *Labyrinthulea* microorganism may be cultured by inoculating it in a suitable medium, and culturing the cells according to an ordinary method.

The medium may be any known medium. Examples of carbon sources include, in addition to carbohydrates such as glucose, fructose, and galactose, oils and fats such as oleic acid, and soybean oil, and glycerol and sodium acetate. The carbon source may be used in a concentration of, for example, 20 to 300 g per liter of medium. In a particularly preferred embodiment, the carbon source may be fed to continue culture after all the carbon sources originally contained in the medium were consumed. By performing culture under these conditions, more carbon source can be consumed, and the yield of 7DHC can increase.

Examples of nitrogen sources include organic nitrogen such as yeast extracts, corn steep liquors, polypeptone, sodium glutamate, and urea, and inorganic nitrogen such as ammonium acetate, ammonium sulfate, ammonium chloride, sodium nitrate, ammonium nitrate, and ammonia.

Mineral salts, such as potassium phosphate, may be used in appropriate combinations.

Preferably, after the medium is prepared, pH thereof is adjusted to the range of 4.0 to 9.5 by adding a suitable acid or base, and then the medium is sterilized with an autoclave.

Preferably, the culture temperature of the *Labyrinthulea* microorganism is controlled to a temperature that allows for 7DHC production. Typically, the culture temperature is 10 to 45° C., preferably 20 to 37° C.

During culturing, pH is typically 3.5 to 9.5, preferably 4.5 to 9.5, most preferably 5.0 to 8.0.

Culture period may be, for example, 2 to 7 days, and the culturing may be performed under aerated stirred conditions.

The *Labyrinthulea* microorganism that has accumulated a high concentration of 7DHC during culture can be obtained in high concentration, typically about 20 to 100 g in terms of a dry cell weight per liter of the medium. Separation of the culture medium and the *Labyrinthulea* microorganism from the culture may be performed by using an ordinary method known to a skilled person, for example, such as centrifugation, and filtration.

The *Labyrinthulea* microorganism separated from culture is homogenized with, for example, an ultrasonic or a Dyno-Mill, and 7DHC can be obtained after solvent extraction with, for example, chloroform, hexane, or butanol. The method for extracting 7DHC and other sterols from the cells of microorganisms is described in L. Parks et al. [Methods in Enzymology 111 Edited (1985) by L Ming, L. Parks, C. Bottema, R. Rodriguez and Thomas Lewis, p. 333-339].

The crude 7DHC thus obtained may be further purified by using a method known to a skilled person, in particular, the method described in Boselli E, Velazco V, Caboni Mf and Lercker G J, Chromatogr A. 2001 May 11; 917 (1-2): 239-44.

It is also possible to use other methods, such as methods used to extract cholesterol from wool. In particular, a skilled person may refer to the methods described in U.S. Pat. Nos. 2,688,623, or 2,650,929, or British Patent No. GB690879, GB646227, or GB613778.

In a preferred embodiment of the present invention, 7DHC is present in *Labyrinthulea* cells in a proportion of more than 5%, preferably more than 10% of the total sterol produced by the *Labyrinthulea* microorganism created by using the method described in Section 2 above.

4. Vitamin D3 Production Process of the Present Invention

A vitamin D3 production process of the present invention is a process for producing vitamin D3 which comprises irradiating the 7DHC produced by the production process of Section 3 above with ultraviolet light.

Vitamin D3 can be produced by irradiating the 7DHC obtained by using the production process of Section 3 above with ultraviolet light, such as with a mercury lamp, followed by heating. The heating temperature is preferably 50 to 100° C., most preferably 80° C. to 100° C. The heating time is preferably 5 to 300 minutes, more preferably 10 to 100 minutes.

The obtained vitamin D3 may be concentrated by using techniques such as high-performance liquid chromatography, and supercritical chromatography, and collected to obtain highly concentrated purified vitamin D3.

Reference Example 1

A Search for *Labyrinthulea* Microorganism that Accumulates Significant Amount of Cholesterol 7DHC has a structure in which a double bond is introduced at carbon 7 of cholesterol. In order to create a *Labyrinthulea* microorganism that produces significant amounts of 7DHC through metabolic modification, it is accordingly desirable that the parent strain is a *Labyrinthulea* microorganism that accumulates significant amount of cholesterol.

To this end, the present inventors examined the cholesterol productivity of *Labyrinthulea* microorganisms deposited at official institutions, as follows.

*Aurantiochytrium* sp. NBRC103268, *Aurantiochytrium* sp. NBRC103269, *Parietichytrium sarkarianum* NBRC104108, *Schizochytrium* sp. ATCC20888, and *Aurantiochytrium limacinum* ATCC MYA-1381 were cultured in evaluation liquid medium (9% glucose, 1% yeast extract, 1% peptone, 50% artificial sea water) at 30° C. for 72 hours.

Lipids were extracted from each culture according to the method of Bligh & Dyer [Bligh E G and Dyer W J, Can. J. Biochem. Physiol. 37 911 (1959)], and dried under reduced pressure. The dry lipids were dissolved in 0.1 N KOH-methanol, and processed at 60° C. for 30 minutes to saponify. For extraction of the free sterols obtained after the saponification process, an equal amount of water was added, and the solution was extracted three times with hexane used in two times the volume of water. The extracted hexane fraction was concentrated under reduced pressure, and analyzed by gas chromatography. For quantification, 5α Cholestane (manufactured by Sigma) was added at an early stage of extraction, and used as internal standard. For cholesterol identification, cholesterol (manufactured by Tokyo Chemical Industry) was used as external standard.

The results are presented in Table 1. As can be seen in Table 1, *Aurantiochytrium limacinum* ATCC MYA-1381 was found to have a high cholesterol producing capability.

[Gas Chromatography Conditions]
Column: HR-52 (Shinwa Chemical Industries Ltd.) 0.25 mm×30 cm, 0.25 mm
Carrier gas: $N_2$, 31 ml/min
Column temperature: 280° C.
Detection: FID

TABLE 1

| *Labyrinthulea* microorganism | (OD 660) | Cholesterol (mg/L) |
|---|---|---|
| NBRC103268 | 14 ± 3.2 | 58 ± 18 |
| NBRC103269 | 30 ± 7.4 | 161 ± 19 |
| NBRC104108 | 3.6 ± 0.2 | 7.6 ± 3.5 |
| ATCC MYA-1381 | 35 ± 05.7 | 205 ± 37 |
| ATCC 20888 | 21 ± 4.9 | 151 ± 4.2 |

Reference Example 2

Identification of DNA Encoding Protein Having SMT Activity of *Labyrinthulea* Microorganism It was confirmed that the DNA having the base sequence represented by SEQ ID NO: 1 encodes a protein having SMT activity by whether the DNA is complementary to the gene (erg6) which encodes a protein having SMT activity of a budding yeast. The details will be described below.

A genomic DNA of a budding yeast S288C strain (obtained from Euroscarf) was prepared by using an ordinary method.

DNA fragments were amplified by PCR, using DNAs consisting of the base sequences denoted as "primer set" in Table 2 as primer sets, and the genomic DNA as a template.

TABLE 2

| Primer set (SEQ ID NO:) | Amplified DNA fragment |
|---|---|
| 3 and 4 | erg6 upstream region |
| 5 and 6 | leu2 gene of budding yeast |
| 7 and 8 | erg6 downstream region |

By using a mixture of these three amplified DNA fragments as a template, PCR was performed using DNAs consisting of the base sequences represented by SEQ ID NOS: 3 and 8 as a primer set. Because SEQ ID NOS: 4 and 5, and SEQ ID NOS: 6 and 7 have complementary sequences at the 5' ends, the three DNA fragments can bind by the PCR. That is, the PCR was performed to prepare a Leu2 expression cassette fragment in which the Leu2 gene of the budding yeast is interposed between an upstream region and a downstream region of erg6.

The Leu2 expression cassette fragment was introduced into a budding yeast BY4742 strain deficient in the Leu2 gene by electroporation. By performing selection using a minimal medium which did not contain leucin, a BY4742Δerg6 strain in which the Leu2 expression cassette fragment was introduced into an erg6 gene region by homologous recombination was obtained. Subsequently, a genomic DNA of *Aurantiochytrium limacinum* ATCC MYA-1381 (hereinafter referred to as "MYA1381") which was found to accumulate a significant amount of cholesterol in Reference Example 1 was prepared by using an ordinary method.

A DNA fragment having the base sequence represented by SEQ ID NO: 1 was amplified by PCR using DNAs consisting of the base sequences represented by SEQ ID NO: 9 (a HindIII recognition sequence was added) and SEQ ID NO: 10 (a XbaI recognition sequence was added) as a primer set and the genomic DNA as a template.

The DNA fragment and a budding yeast expression vector pYes2CT (Life Technologies Japan Ltd.) were treated with HindIII and XbaI, and ligated to each other, and then, *E. coli* DH5α was transformed by using an ordinary method. The obtained plasmid was named "pYes2CT-SMT". pYes2CT-SMT was introduced into the BY4742Δerg6 strain by electroporation. Incidentally, as a control, pYes2CT was also introduced simultaneously. The obtained colony was isolated, suspended in 50 mL of an SCG-Ura medium (0.67% Yeast Nitrogen base without amino acids, 2% galactose, 40 mg/L lysine, 20 mg/L histidine), and cultured for 2 days at 30° C. and 220 rpm. At this time, a strain obtained by introducing pYes2CT into the parent strain BY4742 was also cultured as a control.

After completion of the culturing, the yeast cells were collected by centrifugation at 3000 g for 10 minutes, and lyophilized under reduced pressure. To the lyophilized yeast cells (50 mg), 5 mL of 33% KOH/methanol (1:4 vol/vol) was added, and a treatment was performed at 70° C. for 1 hour. To the liquid after the treatment, 10 mL of hexane was added, and a hexane layer was collected. The hexane layer was subjected to vacuum concentration, and an analysis was performed by gas chromatography mass spectrometry (GCMS2010, manufactured by Shimadzu Corporation).

Figure 1:
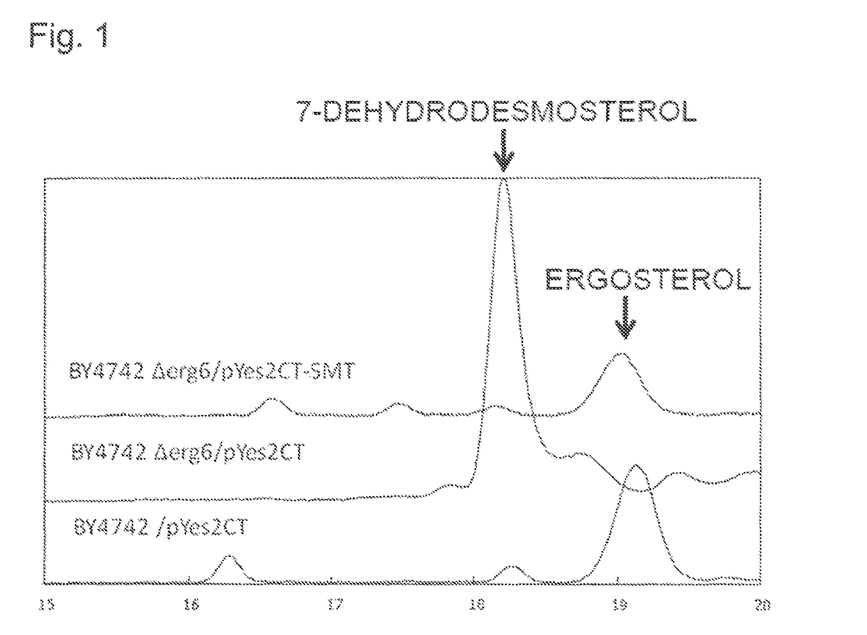
FIG. 1 is a view of gas chromatography showing that a strain obtained by transforming an erg6-deficient budding yeast with a DNA having the base sequence represented by SEQ ID NO: 1 produces and accumulates ergosterol. The horizontal axis represents the retention time (min) in the gas chromatography.

The results are shown in FIG. 1. The BY4742Δerg6/pYes2CT strain did not produce ergosterol, but accumulated 7-dehydrodesmosterol as described in previous reports (Biochem. Biophys. Res. Commun. (1988) 155: 509-517, Metabolic Engineering (2011) 13: 555-569, and JP-A-2012-239412). On the other hand, the BY4742Δerg6/pYes2CT-SMT strain accumulated ergosterol in the same manner as the parent strain in which erg6 was not disrupted. That is, the DNA having the base sequence represented by SEQ ID NO: 1 was complementary to erg6 which encodes the protein having SMT activity of the budding yeast.

From the results, it was found that the DNA having the base sequence represented by SEQ ID NO: 1 encodes the protein (SEQ ID NO: 2) having SMT activity.

Examples of the present invention are shown below, but the present invention is not limited by the following Examples.

Example 1

Creation of *Labyrinthulea* Microorganism in which SMT Activity is Lost

The SMT activity of the MYA1381 strain was eliminated as follows.

DNA fragments were amplified by performing PCR, using DNAs consisting of the base sequences denoted as "primer set" in Table 3 as primer sets, and the genomic DNA of the MYA1381 strain prepared in Reference Example 2 as a template.

TABLE 3

| Primer set (SEQ ID NO: ) | Amplified DNA fragment |
|---|---|
| 11 and 12 | Pyruvate kinase promoter |
| 13 and 14 | Actin terminator |

Further, hygromycin resistant gene was amplified by PCR, using DNAs of the base sequences represented by SEQ ID NOS: 15 and 16 as a primer set, and a drug-resistant gene expression cassette (manufactured by Genebridges) as a template.

By using a mixture of these three amplified DNA fragments as a template, PCR was run using DNAs of the base sequences represented by SEQ ID NOS: 11 and 14 as a primer set. Because SEQ ID NOS: 12 and 15, and SEQ ID NOS: 16 and 13 have complementary sequences at the 5' ends, the three DNA fragments can bind in the PCR. That is, the PCR was performed to prepare an expression cassette fragment of a hygromycin resistant gene having an MYA1381-derived pyruvate kinase promoter and actin terminator.

Each DNA fragment was amplified by PCR, using DNAs of the base sequences denoted as "primer set" in Table 4 as primer sets, and genomic DNA of MYA-1381 as a template. The restriction enzyme sequence described in "Restriction Enzyme Sequence" of Table 4 was added to each DNA fragment.

TABLE 4

| Primer set (SEQ ID NO: ) | Amplified DNA fragment | Restriction enzyme sequence |
|---|---|---|
| 17 and 18 | Upstream region of DNA consisting of base sequence represented by SEQ ID NO: 1 | EcoRI and BamHI |
| 19 and 20 | Downstream region of DNA consistingof base sequence represented by SEQ ID NO: 1 | Sse8387I and BamHI |

The amplified fragment in the upstream region was treated with EcoRI and BamHI, and the amplified fragment in the downstream region was treated with Sse8387I and BamHI, and these were ligated to EcoRI- and Sse8387I-treated pUC18Not vector (Biomedal S.L. Sevilla, Spain) to obtain a plasmid.

The plasmid was treated with BamHI, and ligated to the hygromycin resistant gene expression cassette fragment obtained above which was treated with BamHI. This produced a plasmid in which the hygromycin resistant gene expression cassette was introduced to the upstream and downstream regions of the DNA of the base sequence represented by SEQ ID NO: 1. The plasmid was named pUCSMT-hyg.

The pUCSMT-hyg was treated with NotI to obtain a DNA fragment that had the hygromycin resistant gene expression cassette inserted to the upstream and downstream regions of the DNA consisting of the base sequence represented by SEQ ID NO: 1.

The DNA fragment was introduced into MYA1381 by electroporation to obtain a hygromycin resistant strain. This strain was named MYA1381Δ7DHCR.

It was confirmed by PCR that MYA1381Δ7DHCR had a substitution of the DNA consisting of the base sequence represented with SEQ ID NO: 1 with the DNA fragment having the hygromycin resistant gene expression cassette inserted to the upstream and downstream regions of the DNA consisting of the base sequence represented by SEQ ID NO: 1.

Example 2

Production of 7DHC

The MYA1381 (parent strain) and MYA1381ΔSMT strains were cultured in the same manner as in Reference Example 1, using a liquid medium [0.4% glucose, 0.02% yeast extract, 0.05% sodium glutamate, 50% artificial sea water (DAIGO)].

After the culturing, lipids were extracted from each culture solution according to the method of Bligh & Dyer [Bligh E G and Dyer W J, Can. J. Biochem. Physiol. 37 911 (1959)], and dried under reduced pressure. The dried lipids were dissolved in 0.1 N KOH-methanol, and treated at 60° C. for 30 minutes to perform saponification treatment. For extraction of the free sterols obtained by the saponification treatment, an equal amount of water was added, and extraction was performed three times with hexane in twice the amount of water. The extracted hexane fraction was concentrated under reduced pressure, and an analysis was performed by gas chromatography to examine the amount of the sterols and the composition thereof in the culture solution. For quantification treatment, 5α Cholestane (manufactured by Sigma) was added at an early stage of extraction, and used as internal standard. For cholesterol identification, cholesterol (manufactured by Tokyo Chemical Industry) was used as external standard. The conditions for the gas chromatography were the same as in Reference Example 1.

Figure 2:
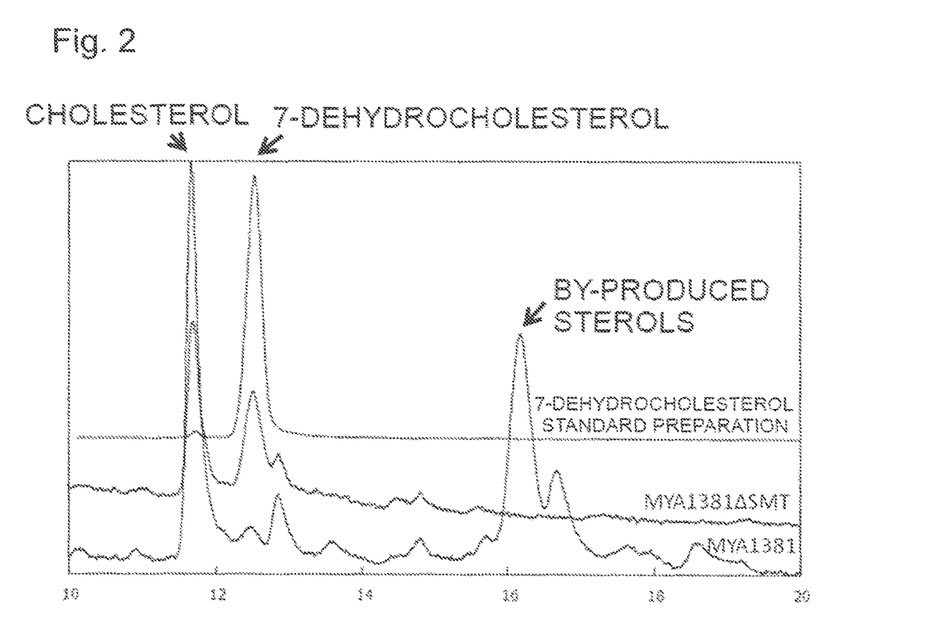
FIG. 2 is a view of gas chromatography showing that a *Labyrinthulea* microorganism in which the SMT activity is lost as compared to a parent strain produces and accumulates 7DHC. The horizontal axis represents the retention time (min) in the gas chromatography.

The results are shown in Table 5 and FIG. 2. In the MYA1381ΔSMT strain, cholesterol which was produced and accumulated in the parent strain was reduced, and 7DHC which was not produced and accumulated in the parent strain was produced and accumulated. Further, by-produced sterols which were produced and accumulated in the parent strain disappeared.

The disappearance of by-produced sterols is considered to work to the advantage of the production of 7DHC, because, for example, it is not necessary to remove the by-produced sterols in a purification step.

TABLE 5

| *Labyrinthulea* microorganism | Cholesterol (mg/L) | 7DHC (mg/L) |
|---|---|---|
| MYA1381 | 3.3 ± 0.5 | 0.0 ± 0.0 |
| MYA1381ΔSMT | 2.0 ± 0.5 | 2.3 ± 0.5 |

Example 3

Production of Vitamin D3

The 7DHC manufactured in Example 2 is irradiated with 300-nm UV light, and processed at 100° C. for 30 minutes.

The product is then analyzed by gas chromatography in the manner described in Reference Example.

INDUSTRIAL APPLICABILITY

According to the present invention, a process for efficiently producing 7DHC using a *Labyrinthulea* microorganism, and a process for producing vitamin D3 comprising irradiating, with ultraviolet light, 7DHC produced by the production process can be provided.

Sequence Listing Free Text

SEQ ID NO: 3—Description of Artificial Sequence: Synthetic DNA
SEQ ID NO: 4—Description of Artificial Sequence: Synthetic DNA
SEQ ID NO: 5—Description of Artificial Sequence: Synthetic DNA
SEQ ID NO: 6—Description of Artificial Sequence: Synthetic DNA
SEQ ID NO: 7—Description of Artificial Sequence: Synthetic DNA
SEQ ID NO: 8—Description of Artificial Sequence: Synthetic DNA
SEQ ID NO: 9—Description of Artificial Sequence: Synthetic DNA
SEQ ID NO: 10—Description of Artificial Sequence: Synthetic DNA
SEQ ID NO: 11—Description of Artificial Sequence: Synthetic DNA
SEQ ID NO: 12—Description of Artificial Sequence: Synthetic DNA
SEQ ID NO: 13—Description of Artificial Sequence: Synthetic DNA
SEQ ID NO: 14—Description of Artificial Sequence: Synthetic DNA
SEQ ID NO: 15—Description of Artificial Sequence: Synthetic DNA
SEQ ID NO: 16—Description of Artificial Sequence: Synthetic DNA
SEQ ID NO: 17—Description of Artificial Sequence: Synthetic DNA
SEQ ID NO: 18—Description of Artificial Sequence: Synthetic DNA
SEQ ID NO: 19—Description of Artificial Sequence: Synthetic DNA
SEQ ID NO: 20—Description of Artificial Sequence: Synthetic DNA

The invention claimed is:

1. A process for producing 7-dehydrocholesterol (hereinafter "7DHC"), comprising:
  culturing, in a medium, a 7DHC-producing *Labyrinthulea* microorganism in which sterol 24-C-methyltransferase activity (hereinafter "SMT activity") is reduced or lost as compared to a parent strain;
  allowing 7DHC to be produced and accumulated in the culture; and
  collecting the 7DHC from the culture,
  wherein the *Labyrinthulea* microorganism in which the SMT activity is reduced or lost as compared to the parent strain is a *Labyrinthulea* microorganism in which the SMT activity is reduced or lost as compared to the parent strain through deletion, substitution, or addition of at least one base in a gene which is present in the chromosomal DNA of the parent strain and encodes a protein having SMT activity, and
  wherein the gene encoding a protein having SMT activity is a gene having any of the following DNAs [1] to [5]:
  [1] a DNA encoding a protein having the amino acid sequence shown by SEQ ID NO: 2;
  [2] a DNA encoding a homologous protein having at least 95% identity with the amino acid sequence shown by SEQ ID NO: 2, and having SMT activity;
  [3] a DNA having the base sequence shown by SEQ ID NO: 1;
  [4] a DNA that hybridizes with a DNA consisting of a base sequence complementary to the base sequence shown by SEQ ID NO: 1 under stringent conditions, and encodes a homologous protein having SMT activity, wherein the stringent conditions comprise conditions in which a filter on which a DNA has been immobilized and a probe DNA are incubated overnight at 42° C. in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l of a denatured salmon sperm DNA, and then the filter is washed in a 0.2×SSC solution at about 65° C.; and
  [5] a DNA having at least 95% identity with the base sequence shown by SEQ ID NO: 1, and encoding a homologous protein having SMT activity.

2. A process for producing 7-dehydrocholesterol (hereinafter "7DHC"), comprising:
  culturing, in a medium, a 7DHC-producing *Labyrinthulea* microorganism in which sterol 24-C-methyltransferase activity (hereinafter "SMT activity") is reduced or lost as compared to a parent strain;
  allowing 7DHC to be produced and accumulated in the culture; and
  collecting the 7DHC from the culture,
  wherein the *Labyrinthulea* microorganism in which the SMT activity is reduced or lost as compared to the parent strain is a *Labyrinthulea* microorganism in which the SMT activity is reduced or lost as compared to the parent strain, being obtained by transforming the parent strain with a DNA encoding an RNA which has a sequence complementary to a messenger RNA transcribed from a gene present in the chromosomal DNA of the parent strain and encoding a protein having SMT activity, and forms a conjugate with the messenger RNA, and
  wherein the gene encoding a protein having SMT activity is a gene having any of the following DNAs [1] to [5]:
  [1] a DNA encoding a protein having the amino acid sequence shown by SEQ ID NO: 2;
  [2] a DNA encoding a homologous protein having at least 95% identity with the amino acid sequence shown by SEQ ID NO: 2, and having SMT activity;
  [3] a DNA having the base sequence shown by SEQ ID NO: 1;
  [4] a DNA that hybridizes with a DNA consisting of a base sequence complementary to the base sequence shown by SEQ ID NO: 1 under stringent conditions, and encodes a homologous protein having SMT activity, wherein the stringent conditions comprise conditions in which a filter on which a DNA has been immobilized and a probe DNA are incubated overnight at 42° C. in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l of a denatured salmon sperm DNA, and then the filter is washed in a 0.2×SSC solution at about 65° C.; and
  [5] a DNA having at least 95% identity with the base sequence shown by SEQ ID NO: 1, and encoding a homologous protein having SMT activity.

3. A process for producing vitamin D3, comprising irradiating the 7DHC produced by the production process according to claim 1 with ultraviolet light.

4. The production process according to claim 2, wherein the *Labyrinthulea* microorganism is a *Labyrinthulea* microorganism of the genus Schizochytorium, *Thraustochytrium, Aurantiochytrium, Parietichytrium*, Labyrinthula, Althornia, Aplanochytrium, Japonochytrium, Labyrinthuloides, *Ulkenia*, Oblongichytrium, *Botryochytrium*, or *Sicyoidochytrium*.

5. The production process according to claim 1, wherein the *Labyrinthulea* microorganism is a *Labyrinthulea* microorganism of the genus Schizochytorium, *Thraustochytrium, Aurantiochytrium, Parietichytrium*, Labyrinthula, Althornia, Aplanochytrium, Japonochytrium, Labyrinthuloides, *Ulkenia*, Oblongichytrium, *Botryochytrium*, or *Sicyoidochytrium*.

6. A process for producing vitamin D3, comprising irradiating the 7DHC produced by the production process according to claim 2 with ultraviolet light.

* * * * *

```
                        SEQUENCE LISTING

<160> NUMBER OF SEQ ID NOS: 20

<210> SEQ ID NO 1
<211> LENGTH: 1005
<212> TYPE: DNA
<213> ORGANISM: Aurantiochytrium limacinum
<220> FEATURE:
<221> NAME/KEY: CDS
<222> LOCATION: (1)..(1005)

<400> SEQUENCE: 1 atg gtg cag ctt tgg gag aag ggc gag aac tac tcg tct gat cag ttc      48
Met Val Gln Leu Trp Glu Lys Gly Glu Asn Tyr Ser Ser Asp Gln Phe
1               5                   10                  15 gtt ggc gcc atc aac tac gcc agc aag aac acc gtg gac aac cag gac      96
Val Gly Ala Ile Asn Tyr Ala Ser Lys Asn Thr Val Asp Asn Gln Asp
                20                  25                  30 gac gag aag aac tac gcc ccc gtt gtg aag agc ttc tac gcc tcc gtt     144
Asp Glu Lys Asn Tyr Ala Pro Val Val Lys Ser Phe Tyr Ala Ser Val
            35                  40                  45 gcc acc agc ctc tac gag tac ggc tgg ggc aag tcc ttc cac ttt gct     192
Ala Thr Ser Leu Tyr Glu Tyr Gly Trp Gly Lys Ser Phe His Phe Ala
        50                  55                  60 ccc cgc aac aag ggt gag ggc ttc cac gcc tct ctc ctc cgc cag gag     240
Pro Arg Asn Lys Gly Glu Gly Phe His Ala Ser Leu Leu Arg Gln Glu
65                  70                  75                  80 cac tgg ctt gcc ggc cag ctc gga atc cgc cct ggc cag gat gtc tgt     288
His Trp Leu Ala Gly Gln Leu Gly Ile Arg Pro Gly Gln Asp Val Cys
                85                  90                  95 gat ctc ggc tgc ggt gtc tgc ggt ccc ctt gtg aac att gcc aag ttc     336
Asp Leu Gly Cys Gly Val Cys Gly Pro Leu Val Asn Ile Ala Lys Phe
            100                 105                 110 acc cgc gcc aac atc acc ggt atc act atc tct gac ttc cag atc gct     384
Thr Arg Ala Asn Ile Thr Gly Ile Thr Ile Ser Asp Phe Gln Ile Ala
        115                 120                 125 cgc ggt aac gcc tgg atc gcc aag aac aac ctc tcc aac cgc tgc aag     432
Arg Gly Asn Ala Trp Ile Ala Lys Asn Asn Leu Ser Asn Arg Cys Lys
```

```
                130             135                 140
gcc atc gag ggt gac ttc cac gag ctc ccc ttc gcg gac aac tcc ttc        480
Ala Ile Glu Gly Asp Phe His Glu Leu Pro Phe Ala Asp Asn Ser Phe
145                 150                 155                 160 gat gcc ggt tac gac atg gag gcc act gcc cac tcc act aag ctc aac        528
Asp Ala Gly Tyr Asp Met Glu Ala Thr Ala His Ser Thr Lys Leu Asn
                165                 170                 175 cag ttc ttc tct gag gtt cac cgt gtg ctc cgc ccc ggt ggt gtc ttc        576
Gln Phe Phe Ser Glu Val His Arg Val Leu Arg Pro Gly Gly Val Phe
            180                 185                 190 ggt ggc ttc gcc tgg gtg acc ctc ccc aag tac aac ccg gaa gac aag        624
Gly Gly Phe Ala Trp Val Thr Leu Pro Lys Tyr Asn Pro Glu Asp Lys
        195                 200                 205 gtc gag aag aag atc ctc gat gac ctc gcc ttc tcc aac gct att gcc        672
Val Glu Lys Lys Ile Leu Asp Asp Leu Ala Phe Ser Asn Ala Ile Ala
    210                 215                 220 atc ctt cac agc ttc gac gac tac gtc gcc gcc atc aaa gca aac cct        720
Ile Leu His Ser Phe Asp Asp Tyr Val Ala Ala Ile Lys Ala Asn Pro
225                 230                 235                 240 ggt ctt gag ctc gtt gag gcc tac gat gcc aac aag ctc ggc gac gac        768
Gly Leu Glu Leu Val Glu Ala Tyr Asp Ala Asn Lys Leu Gly Asp Asp
                245                 250                 255 ttc gag tgg tac gac ccc ctc cag cct ggc ttc tcc ctc gag ggt atc        816
Phe Glu Trp Tyr Asp Pro Leu Gln Pro Gly Phe Ser Leu Glu Gly Ile
            260                 265                 270 ctc cgc tct tgg gct ggc cgc cag ttc acc tct gtt ttg acc cgc atc        864
Leu Arg Ser Trp Ala Gly Arg Gln Phe Thr Ser Val Leu Thr Arg Ile
        275                 280                 285 acc gag gcc atc ggc ctt gcc ccc aag ggt acc tac cag gct tcc cag        912
Thr Glu Ala Ile Gly Leu Ala Pro Lys Gly Thr Tyr Gln Ala Ser Gln
    290                 295                 300 gtt ctc gag atc gct gcc cag tcc ctc gtt gag tcc ggt gtc cgc ggt        960
Val Leu Glu Ile Ala Ala Gln Ser Leu Val Glu Ser Gly Val Arg Gly
305                 310                 315                 320 atc tac acc ccc atc tac tac tac aag gtc cga aag gtc tcc aac          1005
Ile Tyr Thr Pro Ile Tyr Tyr Tyr Lys Val Arg Lys Val Ser Asn
                325                 330                 335

<210> SEQ ID NO 2
<211> LENGTH: 335
<212> TYPE: PRT
<213> ORGANISM: Aurantiochytrium limacinum

<400> SEQUENCE: 2

Met Val Gln Leu Trp Glu Lys Gly Glu Asn Tyr Ser Ser Asp Gln Phe
1               5                   10                  15

Val Gly Ala Ile Asn Tyr Ala Ser Lys Asn Thr Val Asp Asn Gln Asp
            20                  25                  30

Asp Glu Lys Asn Tyr Ala Pro Val Val Lys Ser Phe Tyr Ala Ser Val
        35                  40                  45

Ala Thr Ser Leu Tyr Glu Tyr Gly Trp Gly Lys Ser Phe His Phe Ala
    50                  55                  60

Pro Arg Asn Lys Gly Glu Gly Phe His Ala Ser Leu Leu Arg Gln Glu
65                  70                  75                  80

His Trp Leu Ala Gly Gln Leu Gly Ile Arg Pro Gly Gln Asp Val Cys
                85                  90                  95

Asp Leu Gly Cys Gly Val Cys Gly Pro Leu Val Asn Ile Ala Lys Phe
            100                 105                 110
```

Thr Arg Ala Asn Ile Thr Gly Ile Thr Ile Ser Asp Phe Gln Ile Ala
            115                 120                 125

Arg Gly Asn Ala Trp Ile Ala Lys Asn Leu Ser Asn Arg Cys Lys
130                 135                 140

Ala Ile Glu Gly Asp Phe His Glu Leu Pro Phe Ala Asp Asn Ser Phe
145                 150                 155                 160

Asp Ala Gly Tyr Asp Met Glu Ala Thr Ala His Ser Thr Lys Leu Asn
                165                 170                 175

Gln Phe Phe Ser Glu Val His Arg Val Leu Arg Pro Gly Gly Val Phe
            180                 185                 190

Gly Gly Phe Ala Trp Val Thr Leu Pro Lys Tyr Asn Pro Glu Asp Lys
            195                 200                 205

Val Glu Lys Lys Ile Leu Asp Asp Leu Ala Phe Ser Asn Ala Ile Ala
210                 215                 220

Ile Leu His Ser Phe Asp Asp Tyr Val Ala Ala Ile Lys Ala Asn Pro
225                 230                 235                 240

Gly Leu Glu Leu Val Glu Ala Tyr Asp Ala Asn Lys Leu Gly Asp Asp
                245                 250                 255

Phe Glu Trp Tyr Asp Pro Leu Gln Pro Gly Phe Ser Leu Glu Gly Ile
            260                 265                 270

Leu Arg Ser Trp Ala Gly Arg Gln Phe Thr Ser Val Leu Thr Arg Ile
            275                 280                 285

Thr Glu Ala Ile Gly Leu Ala Pro Lys Gly Thr Tyr Gln Ala Ser Gln
            290                 295                 300

Val Leu Glu Ile Ala Ala Gln Ser Leu Val Glu Ser Gly Val Arg Gly
305                 310                 315                 320

Ile Tyr Thr Pro Ile Tyr Tyr Lys Val Arg Lys Val Ser Asn
                325                 330                 335

<210> SEQ ID NO 3
<211> LENGTH: 28
<212> TYPE: DNA
<213> ORGANISM: Artificial Sequence
<220> FEATURE:
<223> OTHER INFORMATION: Synthetic DNA

<400> SEQUENCE: 3
gctcgctatc ctcgccatca cgtgtacc                                28

<210> SEQ ID NO 4
<211> LENGTH: 57
<212> TYPE: DNA
<213> ORGANISM: Artificial Sequence
<220> FEATURE:
<223> OTHER INFORMATION: Synthetic DNA

<400> SEQUENCE: 4
actagaagtt ctcctcgact taaatcgaaa gtaaaacaga taagggaaac ttgaatg      57

<210> SEQ ID NO 5
<211> LENGTH: 45
<212> TYPE: DNA
<213> ORGANISM: Artificial Sequence
<220> FEATURE:
<223> OTHER INFORMATION: Synthetic DNA

<400> SEQUENCE: 5
actttcgatt taagtcgagg agaacttcta gtatatctac atacc               45

<210> SEQ ID NO 6
<211> LENGTH: 45
<212> TYPE: DNA
<213> ORGANISM: Artificial Sequence
<220> FEATURE:
<223> OTHER INFORMATION: Synthetic DNA

<400> SEQUENCE: 6
actttcgatt taagtcgagg agaacttcta gtatatctac atacc             45

<210> SEQ ID NO 7
<211> LENGTH: 45
<212> TYPE: DNA
<213> ORGANISM: Artificial Sequence
<220> FEATURE:
<223> OTHER INFORMATION: Synthetic DNA

<400> SEQUENCE: 7
ttattgagtt gctcgactac gtcgttaagg ccgtttctga cagag             45

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
ggtggtaaca gtacatgggg aggtcattaa tc                           32

<210> SEQ ID NO 9
<211> LENGTH: 37
<212> TYPE: DNA
<213> ORGANISM: Artificial Sequence
<220> FEATURE:
<223> OTHER INFORMATION: Synthetic DNA

<400> SEQUENCE: 9
cccaagctta acacaatggt gcagctttgg gagaagg                      37

<210> SEQ ID NO 10
<211> LENGTH: 36
<212> TYPE: DNA
<213> ORGANISM: Artificial Sequence
<220> FEATURE:
<223> OTHER INFORMATION: Synthetic DNA

<400> SEQUENCE: 10
gctctagatt agttggagac ctttcggacc ttgtag                       36

<210> SEQ ID NO 11
<211> LENGTH: 33
<212> TYPE: DNA
<213> ORGANISM: Artificial Sequence
<220> FEATURE:
<223> OTHER INFORMATION: Synthetic DNA

<400> SEQUENCE: 11
cgggatccaa tgcaatgtaa tgcagtgcaa tgc                          33

<210> SEQ ID NO 12
<211> LENGTH: 45
<212> TYPE: DNA
<213> ORGANISM: Artificial Sequence
<220> FEATURE:
<223> OTHER INFORMATION: Synthetic DNA

<400> SEQUENCE: 12
gcggtgagtt caggcttttt catcttcgag caagcctttg cacag    45

<210> SEQ ID NO 13
<211> LENGTH: 45
<212> TYPE: DNA
<213> ORGANISM: Artificial Sequence
<220> FEATURE:
<223> OTHER INFORMATION: Synthetic DNA

<400> SEQUENCE: 13
cgacgccccg gatgacacgt cattggagtg atggaatgcc ctctc    45

<210> SEQ ID NO 14
<211> LENGTH: 34
<212> TYPE: DNA
<213> ORGANISM: Artificial Sequence
<220> FEATURE:
<223> OTHER INFORMATION: Synthetic DNA

<400> SEQUENCE: 14
cgggatccgg acgtgattgc tacatcataa agcg    34

<210> SEQ ID NO 15
<211> LENGTH: 42
<212> TYPE: DNA
<213> ORGANISM: Artificial Sequence
<220> FEATURE:
<223> OTHER INFORMATION: Synthetic DNA

<400> SEQUENCE: 15
gcaaaggctt gctcgaagat gaaaaagcct gaactcaccg cg    42

<210> SEQ ID NO 16
<211> LENGTH: 45
<212> TYPE: DNA
<213> ORGANISM: Artificial Sequence
<220> FEATURE:
<223> OTHER INFORMATION: Synthetic DNA

<400> SEQUENCE: 16
atcactccaa tgacgtgtca tccggggcgt cggtttccac tatcg    45

<210> SEQ ID NO 17
<211> LENGTH: 41
<212> TYPE: DNA
<213> ORGANISM: Artificial Sequence
<220> FEATURE:
<223> OTHER INFORMATION: Synthetic DNA

<400> SEQUENCE: 17
cggaattcga ttgattgact tcttattgtt tgcatggtct c    41

<210> SEQ ID NO 18
<211> LENGTH: 44
<212> TYPE: DNA
<213> ORGANISM: Artificial Sequence
<220> FEATURE:
<223> OTHER INFORMATION: Synthetic DNA

<400> SEQUENCE: 18
cgggatccat tatactatgt ggttgttgta ctttgaatgt tcac    44

<210> SEQ ID NO 19
<211> LENGTH: 42

```
<212> TYPE: DNA
<213> ORGANISM: Artificial Sequence
<220> FEATURE:
<223> OTHER INFORMATION: Synthetic DNA

<400> SEQUENCE: 19
cgggatccgg tccgaaaggt ctccaactaa aattgtgtaa cg                           42

<210> SEQ ID NO 20
<211> LENGTH: 45
<212> TYPE: DNA
<213> ORGANISM: Artificial Sequence
<220> FEATURE:
<223> OTHER INFORMATION: Synthetic DNA

<400> SEQUENCE: 20
atatgccctg caggaaagca agcgtggaat aagccatcgg aagtg                        45
```